(12) United States Patent
Ow-Wing

(10) Patent No.: US 8,372,351 B2
(45) Date of Patent: Feb. 12, 2013

(54) GLUCOSE MONITORING SYSTEM WITH WIRELESS COMMUNICATIONS

(75) Inventor: Kevin M. Ow-Wing, Castro Valley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 255 days.

(21) Appl. No.: 12/789,721

(22) Filed: May 28, 2010

(65) Prior Publication Data

US 2010/0305421 A1 Dec. 2, 2010

Related U.S. Application Data

(60) Provisional application No. 61/182,460, filed on May 29, 2009.

(51) Int. Cl.
*G01N 33/00* (2006.01)
(52) U.S. Cl. .................. 422/403; 422/400; 422/68.1
(58) Field of Classification Search .................. 422/400, 422/403, 68.1
See application file for complete search history.

(56) References Cited

U.S. PATENT DOCUMENTS

2002/0002326 A1* 1/2002 Causey et al. ............... 600/300
2007/0233395 A1 10/2007 Neel
2008/0281179 A1 11/2008 Fennell et al.

FOREIGN PATENT DOCUMENTS

EP 1837787 A1 9/2007
WO 2005/074161 A1 8/2005

OTHER PUBLICATIONS

Jaap C. Haartsen et al: "Bluetooth—A New Low-Power Radio Interface Providing Short-Range Connectivity", Proceedings of the IEEE, IEEE, New York, U.S. vol. 88, No. 10, Oct. 1, 2000 XP011044431, ISSN: 0018-9219; ISBN: 978-1-4244-5213-4.

* cited by examiner

*Primary Examiner* — Sam P Siefke
(74) *Attorney, Agent, or Firm* — Thomas A. Runk; Fulwider Patton LLP

(57) ABSTRACT

A glucose monitor having only a test strip reader and wireless transmission to a remote hand held calculation processor. All glucose data processing occurs in a remote hand held calculator processor with the glucose monitor providing only sensing and wireless transfer of data. In an embodiment, the glucose monitor includes a button for use in wirelessly pairing the monitor to a smart phone for data communication with a non-proprietary communication protocol, and a light source to communicate the progress of the pairing. In a further embodiment, the glucose monitor includes a switch coupled to the strip reader such that power is applied to the monitor when a test strip is inserted and power is removed with the withdrawal of the test strip. In another embodiment, inserting the test strip and activating the switch also places the glucose monitor into the pairing search mode to communication with a host remote processor.

22 Claims, 6 Drawing Sheets

GLUCOSE MONITORING SYSTEM WITH WIRELESS COMMUNICATIONS

CROSS-REFERENCE TO RELATED APPLICATION

This application claims the benefit of U.S. Patent Application No. 61/182,460, filed on May 29, 2009, which is incorporated herein by reference.

BACKGROUND OF THE INVENTION

The present invention relates to diabetes management and more particularly, to glucose monitoring, wireless communication of glucose data, and glucose data processing.

A diabetes mellitus management system typically includes chemically active, disposable test strips that measure a characteristic of the blood to determine the level of glucose, a glucose measuring device or "strip reader," a medication delivery device such as an insulin pump, and a processor that performs calculations based on the measured glucose and various other user parameters, such as insulin-on-board, a meal event, an exercise event, and others. The glucose strip readers are often implemented in devices that contain numerous other hardware elements, such as computing, processing, display, and/or memory components. While such additional capability can be helpful to users, the inclusion of such elements generally adds significant additional size and manufacturing complexity to any device into which these elements are integrated.

For the benefit of users, diabetes management devices should be kept as small and light-weight as possible so that they do not over-burden the user. It has been found that larger and heavier devices are undesirable to most users since they may be more visible to others, more difficult to attach to the user in an operational position, and a constant visual and tactile reminder of the severe medical problem the user faces on a day-to-day basis. It is a goal to provide lighter and smaller components so that they do not become relegated to non-use. Additionally, devices incorporating processing components can be large in size, complex and costly to produce, and consequently not marketable to a broad range of people affected by diabetes. It is therefore a goal to achieve as much efficiency as possible so that smaller size devices may be produced.

It would be desirable therefore, to judiciously locate necessary management system functions among the various devices of a medical system in a more efficient manner so that the components of the system can be more efficiently employed for the user's care. For example, a re-evaluation of the locations for glucose data processing may result in much of the processing moved to a single device, as opposed to spreading it among a plurality of devices with the accompanying increase in complexity for each one.

It then becomes a decision of where to locate the required components of a diabetes management system. For example, glucose monitors that are used to measure, or read, the glucose level of a drop of blood deposited on a glucose test strip must be used in one form or another and their data changed to a digital format. This is often performed at the same location since analog-to-digital converters are often built into sensors. However, it may not be necessary to process that sensor data and provide a display of that processed data at that location. Since strip readers are used to perform the mechanical function of receiving a test strip in a particular location with a particular orientation, as well as possibly perform electrical and chemical tests, depending on the blood measuring technology used, they may have a shorter life span than other components of a diabetes management system, and may need to be replaced more often. Minimizing the glucose monitor/strip reader functions may therefore result in a lower cost, smaller size, and more efficiency in data processing. Changes to make them less complex and costly may result in their becoming disposable.

Additionally, data is often transferred by wireless means between a monitor and a remote host processor having a display. Proprietary transmission protocols are often used that result in the ability to use only certain hardware. This limits the options of a user and may lower efficiency in managing diabetes. It would be an advantage if more functions in glucose monitoring and diabetes management were performed by software that is run on widely available hardware using non-proprietary wireless data transmission protocols.

Hence those skilled in the art have recognized a need for reducing the size of various components in a diabetes management system. A need has also been recognized by those of skill in the art for increasing efficiency while reducing the number of locations for processing glucose data, thereby consolidating functions into fewer areas. Reduction in manufacturing complexity and cost are also needs recognized by those of skill in the art. A further need has also been recognized for the use of non-proprietary wireless data transmission protocols so that more widely available hardware may be usable. The present invention fulfills these needs and others.

SUMMARY OF THE INVENTION

The invention is directed to a glucose monitor having minimal components in the monitor itself with data processing shifted to a host calculation processor. There is provided a portable glucose monitor comprising a glucose sensor that senses a glucose level and provides glucose sensor data representative of the level of glucose sensed, a glucose monitor processor configured to receive the glucose sensor data, process the received glucose data to the limited extent of automatically adjusting it as necessary in accordance with a characteristic of a test strip, and provide such processed glucose data for transmission, a wireless communication component including a transmitter configured to receive the processed glucose data and wirelessly transmit the processed glucose data by a predetermined protocol, and a portable housing in which are located only the glucose sensor, the glucose data processor, and the communication component and including no direct user interface other than the glucose sensor.

In more detailed aspects, the communication component is further configured to wirelessly pair itself with a remote host processor such that the wireless transmission of the processed glucose data is made from the glucose monitor only to a paired remote host processor. Further, the glucose sensor includes a switch located so as to be activated by the action of introducing a test strip from the glucose sensor wherein when the switch is activated by introducing a test strip into the glucose sensor, the glucose monitor automatically enters the pairing mode in which it performs pairing functions to pair with a remote processor.

In another aspect, the glucose sensor also includes a switch located so as to be activated and de-activated by the action of inserting and withdrawing a test strip from the glucose sensor wherein, when the switch is activated by introducing a test strip into the glucose sensor, the glucose monitor becomes powered up for full operation and wherein, when the switch is de-activated by withdrawing a test strip from the glucose sensor, the glucose monitor is powered down to less than full operation. Also, when powered down to less than full operation, the communication module remains paired with a remote processor until the remote processor unpairs the two from its end.

In additional aspects, the glucose data processor is not configured to determine or display a glucose level from the glucose data. The monitor further comprises a temperature sensor located within the housing to provide temperature data of the temperature at the housing. The glucose processor is further configured to receive the temperature data and provide it to the communication component. The communication module is further configured to directly receive the temperature data from the glucose processor and wirelessly transmit the temperature data by a predetermined protocol.

In more detailed aspects, there is provided a diabetes management system comprising a portable glucose monitor including a glucose sensor that senses a glucose level and provides glucose sensor data representative of the level of glucose sensed; a glucose monitor processor configured to receive the glucose sensor data, process the received glucose data to the limited extent of automatically adjusting it as necessary in accordance with a characteristic of a test strip, and provide such processed glucose data for transmission; a wireless communication component including a transmitter configured to receive the processed glucose data and wirelessly transmit the processed glucose data by a predetermined protocol; a portable housing in which are located only the glucose sensor, the glucose data processor, and the communication component and including no direct user interface other than the glucose sensor; and a remote host calculation device including: a remote host communication module configured to wirelessly pair with a portable glucose monitor so that data communications between the two may occur; a display; a remote host processor; and a memory in which is stored a host glucose data processing program which when run, configures the host processor to analyze glucose data received from the glucose sensor, determine a glucose level, display the determined glucose level, and provide a calculated action on the display in response to the determined glucose level.

In further aspects related to the diabetes management system, the calculated action display by the host program includes a recommended dose of medication. The glucose processing program further configures the remote processor to time and date stamp the glucose data received. The remote host calculation device comprises a smart phone having the host glucose data processing program as a downloadable application program. The host glucose data processing program is configured to allow a user to input a manual coding for a test strip. The glucose monitor includes no user interface other than a test strip reader.

Additionally, in other aspects, the host calculation device further comprises a wireless pairing program configured to enable the remote host calculation device to perform a complete pairing procedure with a glucose monitor that has no pairing switch. The glucose monitor includes a test strip switch which, when activated by the insertion of a test strip, automatically activates a wireless pairing feature in the glucose monitor to enable the glucose monitor to be paired with the remote host calculation device; and the host calculation device further comprises a wireless pairing program configured to enable the remote host calculation device to perform a pairing procedure with a glucose monitor that is performing a pairing procedure when the test strip switch has been activated.

In other aspects there is provided a portable glucose monitor comprising a glucose sensor that senses a glucose level and provides glucose sensor data representative of the level of glucose sensed, a glucose monitor processor configured to receive the glucose sensor data, process the received glucose data to the limited extent of automatically adjusting it as necessary in accordance with a characteristic of a test strip, and provide such processed glucose data for transmission, a temperature sensor providing temperature data representative of the temperature at the glucose sensor, a pairing switch, an indicator device, a wireless communication component including a transmitter configured to receive the processed glucose data and wirelessly transmit the processed glucose data and temperature data by a predetermined protocol, the communication component responsive to the pairing switch to initiate a wireless pairing procedure to pair with a host processor, the communication component causing activation of the indicator device to indicate the status of the pairing procedure, and a portable housing in which are located only the glucose sensor, the temperature sensor, the glucose data processor, and the communication component and including no direct user interface other than the glucose sensor.

The features and advantages of the invention will be more readily understood from the following detailed description which should be read in conjunction with the accompanying drawings.

BRIEF DESCRIPTION OF THE DRAWINGS

The accompanying drawings, which constitute a part of this specification, illustrate various embodiments and aspects of the present invention and, together with the description, explain the principles of the invention. In the drawings.

DETAILED DESCRIPTION OF PREFERRED EMBODIMENTS

Figure 1:
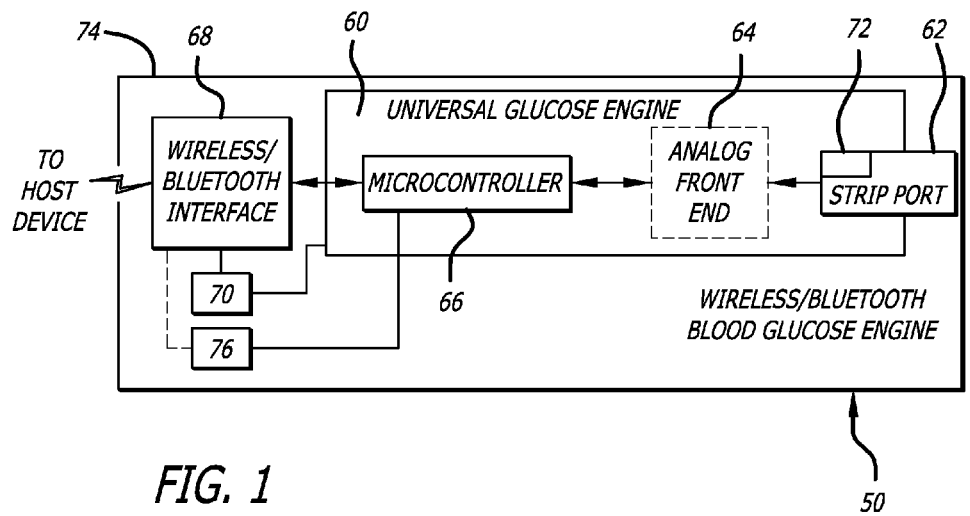
FIG. 1 is a block diagram of a self-contained portable glucose monitor for receiving a glucose test strip, reading the amount of glucose on that test strip, providing data representative of the amount of measured glucose, processing the glucose data into a predetermined wireless communication protocol, and wirelessly communicating that measured data, the monitor having a temperature sensor and no user interface other than the insertion of a test strip.

Reference will now be made in more detail to the drawings in which like reference numerals are used to indicate like or similar elements or components among the several views. Turning now to FIG. 1, there is shown a block diagram of a self-contained portable glucose monitor 50 that includes a strip reader 62 having a port for receiving a glucose test strip to measure glucose content in a drop of blood that was deposited onto that test strip (not shown). The glucose monitor 50 also contains a microcontroller 66, also referred to herein as a glucose sensor processor, connected to the strip reader. An analog-to-digital (A/D) converter 64 converts the output of the glucose strip reader into digital signals. The A/D converter 64 may be a part of the glucose strip reader 62, a separate element, part of the microcontroller 66, or may have other well-known configurations.

The microcontroller 66 receives the digital glucose data and if automatic coding of the test strips is available, will apply such adjustment as necessary in accordance with the particular coding. In the case of the embodiment of FIG. 1, manual coding is not available and must be done at a remote calculator processor.

The microcontroller will then pass the digital glucose data representative of the level of glucose on the test strip to the communication module 68 where the glucose data is processed into a suitable form for wireless transmission in accordance with a predetermined protocol, such as blue tooth. In another embodiment, the microcontroller 66 analyzes the test strip glucose data to determine the glucose level on the test strip, which may also be referred to "glucose data." The glucose data is then transmitted via the wireless/Bluetooth interface 68 to a remote host device. The blood glucose sensor device further contains a power source 70 in this embodiment to power to the device.

In this embodiment, the wireless/Bluetooth interface 68 uses a non-proprietary wireless communication protocol, an example of which is Bluetooth. This enables a wide variety of programmable host devices to be used and to function as the "meter" of the system while the glucose monitor functions only as a sensor with wireless capability. Many devices today are capable of Bluetooth communications and if they are programmable, they may be configured to receive and process the glucose data and display results and recommended actions to the user.

FIG. 1 also presents the test strip reader 62 with a switch 72. Upon inserting a test strip into the port of the strip reader, the switch 72 will be activated. Upon withdrawing a test strip from the port of the strip reader, the switch 72 will be deactivated in this embodiment. Other embodiments are possible including the use of a latching switch 72. As will be discussed below, activation and deactivation of the switch may be used for multiple purposes. In one case, activation of the switch 72 may cause power 70 to be applied to the glucose monitor 50 to put the glucose monitor into the fully operational configuration. Withdrawing the test strip and deactivating the switch will have the opposite effect. In another embodiment or feature, inserting a test strip into the port of the strip reader 62 and thereby activating the switch will cause the wireless interface module 68 to search for a paired remote processor. Withdrawing a test strip and thereby deactivating the switch will cause the wireless interface 68 to drop communications with a paired remote processor.

Additionally, FIG. 1 includes a temperature sensor 76 for sensing the temperature at the location of the glucose sensor 60. The temperature sensor 76 provides temperature data representative of the temperature sensed. In one embodiment, that temperature data are provided to the microcontroller 66 for formatting and further output to the wireless interface 68 for wireless transmission to the host device. In another embodiment, the temperature data are provided directly (dashed lines) to the wireless interface 68 for wireless transmission to the host device.

The components discussed above for FIG. 1 are all included in a single housing 74. In view of the small number of components inside the housing and the fact that all components may be quite small (the power supply 70 may be the largest component), the glucose monitor 50 of FIG. 1 may be disposable. Since all major processing of the glucose data is performed elsewhere, and the fact that this monitor embodiment may be made in large quantities, disposability is possible. In accordance with the approach of aspects of the invention, the user interface application, memory, display, and other major elements of the glucose data processing activity have been shifted elsewhere. The glucose monitor 50 therefore may be made in a manner that results in disposability after a certain number of uses.

Figure 2:
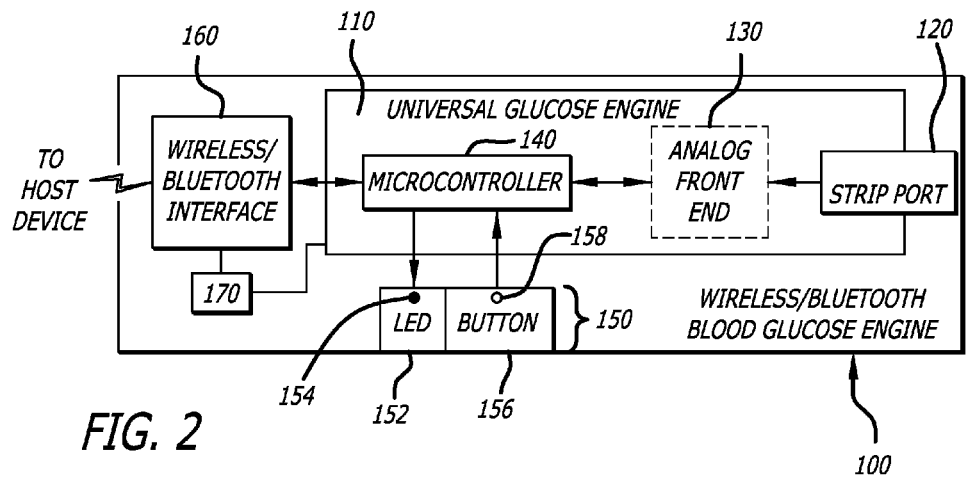
FIG. 2 is a block diagram of an alternate embodiment of a self-contained portable glucose monitor similar to that of FIG. 1 but for the inclusion of additional user interface components of a button and an indicator for limited control over the measurement device.

FIG. 2 illustrates an alternate embodiment of a self-contained blood glucose sensor device 100. In particular, the glucose monitor 100 comprises a blood glucose measuring or acquisition component 120, such as a strip reader, that obtains blood glucose data from an inserted test strip and outputs that glucose data, a glucose sensor processor 140 (microcontroller) that processes the glucose value to, for example, prepare associated blood glucose data for transmission, and a communication component 160 including a transmitter configured to transmit the blood glucose data to another (second/host) computing device. In one exemplary implementation, the transmitter transmits via one or more non-proprietary wireless communication protocols, such as Bluetooth, to a remote second/host processing component for subsequent processing or re-transmission of the glucose data.

According to some implementations, the glucose measuring or acquisition component 120 may comprise a glucose strip reader or testing port (strip port as discussed above) that receives a glucose test strip on which user blood or other fluid is placed. Further implementations may also include a converting component 130 such as an analog-to-digital converter that receives an analog signal from the strip reader and converts it to digital glucose data suitable for subsequent processing and transmission. Indeed, further innovation associated with usage of a low-cost analog front end, here (62 and 130) exists via implementations involving test strips that provide an analog glucose output signal based on certain electrical/electrochemical characteristics (e.g., coulometric, amperometric, etc.) of aspects of the strip; see, e.g., aspects of U.S. Pat. Nos. 4,545,382; 4,711,245; 5,509,410; 5,628,890; 5,820,551; 6,067,463; 6,071,391; 6,120,676; 6,143,164; 6,175,752; 6,299,757; 6,338,790; 6,377,894; 6,461,496; 6,503,381; 6,514,718; 6,540,891; 6,591,125; 6,592,745; 6,600,997; 6,616,819; 6,618,934; 6,676,816; 6,730,200; 6,736,671; 6,736,957; 6,749,740; 6,764,581; 6,773,671; 6,893,545; 6,942,518; 7,504,019; U.S. patent application publication Nos. US2006/0025662; US2006/0064035; US2006/0091006; US2007/0068807; US2007/0095661; US2007/0108048; US2007/0199818; US2007/0227911; US2008/0066305; US2008/0101983; US2008/0102441; US2008/0119702; US2008/0119710; US2008/0148873; US2008/0230384; US2008/0264787; US2008/0267823; US2009/0000959; US2009/0014328; US2009/0095625; and U.S. patent application Ser. Nos. 11/461,725, filed Aug. 1, 2006, and 12/102,374, filed Apr. 14, 2008, which are incorporated herein by reference in entirety.

The portable glucose monitor 100 of this embodiment may also include various input/output elements or indicia 150 by way of a user interface. By way of example and not limitation, the glucose monitor 100 may comprise a visible output element 152, such as a display, interface, GUI, graphic element, one or more light-emitting diodes 154 (LEDs), and/or other audible or tactile (e.g., vibrating, etc.) output indicators, etc. Further, a glucose monitor 100 may also include various input elements 156, such as buttons 158, keys, keyboards, or other user-activated input mechanisms relating to touch, voice, or other, the use of which is discussed below.

The output element 152 and input element 156 provide an active user interface to the glucose monitor 100 in that the user can control at least one action of the monitor with the button 156 and can see actions of the monitor with the illumination devices 152. If the glucose monitor 100 had only an illumination device 156 or devices and no button, the interface would be considered to be passive since the user has no control over the glucose monitor's actions at the glucose monitor itself. In the case of the glucose monitor 50 of FIG. 1, there are neither output nor input elements that the user can see or manipulate, and thus the user interface with that glucose monitor 50 is passive. The effect of the user inserting a test strip into the strip reader 62 and the glucose monitor 50 powering up is done automatically by an internal switch 72 that the user has no control over. Therefore, the interface is still considered to be passive.

In one exemplary implementation, a glucose monitor 100 may be configured for wireless communication to a portable/mobile computing device, phone (such as a "smart phone"), PDA, or other similar device, serving as the second/host computing component. Here, for example, the monitor 100 may connect wirelessly via a non-proprietary wireless protocol, such as by a Bluetooth communications protocol, to a device such as a smart phone. Such a Bluetooth-enabled glucose monitor device 100 may be implemented with a strip port 120 that accepts glucose test strips (such as FreeStyleO test strips for use in blood glucose monitoring or Precision© brand test strips for use in monitoring glucose and ketones. FreeStyleO and PrecisionO brand analyte test strips are available from Abbott Diabetes Care Inc., Alameda, Calif.) to acquire user glucose values.

Here then the smart phone/host device will run an associated application program, as set forth below, and may also provide one or more of: a memory for storage of data or results, one or more processing components that process and/or re-transmit the relevant glucose data, a user interface for displaying data/results, and/or a clock for providing timestamp information, among other elements typically resident on such devices. In one advantageous implementation as shown in FIG. 1, an exemplary Bluetooth blood glucose monitor or engine (also referred to as "BGE" standing for blood glucose engine) meter is configured to only provide glucose and temperature values to the host/smart phone device. At various places herein, the glucose monitors 50 (FIG. 1) and 100 (FIG. 2) may be referred to as monitors, devices, or measurement devices with the same meaning.

Consistent with the implementations herein, the present innovations minimize glucose monitor cost by having the user interface located on the remote host device and/or other dedicated components (such as associated hardware and/or processing, memory, display, etc. elements), thus allowing the glucose monitor to be smaller and less costly. Implementations herein may also allow anyone with a smart host device having a non-proprietary wireless communication protocol such as Bluetooth to utilize extensive blood glucose metering functionality on the host, as the meter capabilities are no longer the constraint on the feature set on the monitor. In conjunction with a Bluetooth-capable smart host device such as a cellular phone for example, implementations herein provide the ability to provide glucose metering with minimal expense and complication.

In a further implementation, glucose monitors 50 and 100 may be configured to turn on or "wake up" and establish or re-establish the wireless link with the host device upon insertion of a glucose test strip into the strip port 62. Such a device may also be configured to turn off or enter a sleep mode when the results have been obtained, when the glucose data has been transmitted (receipt confirmed), and/or when a test strip is removed from the strip port.

Figure 3:
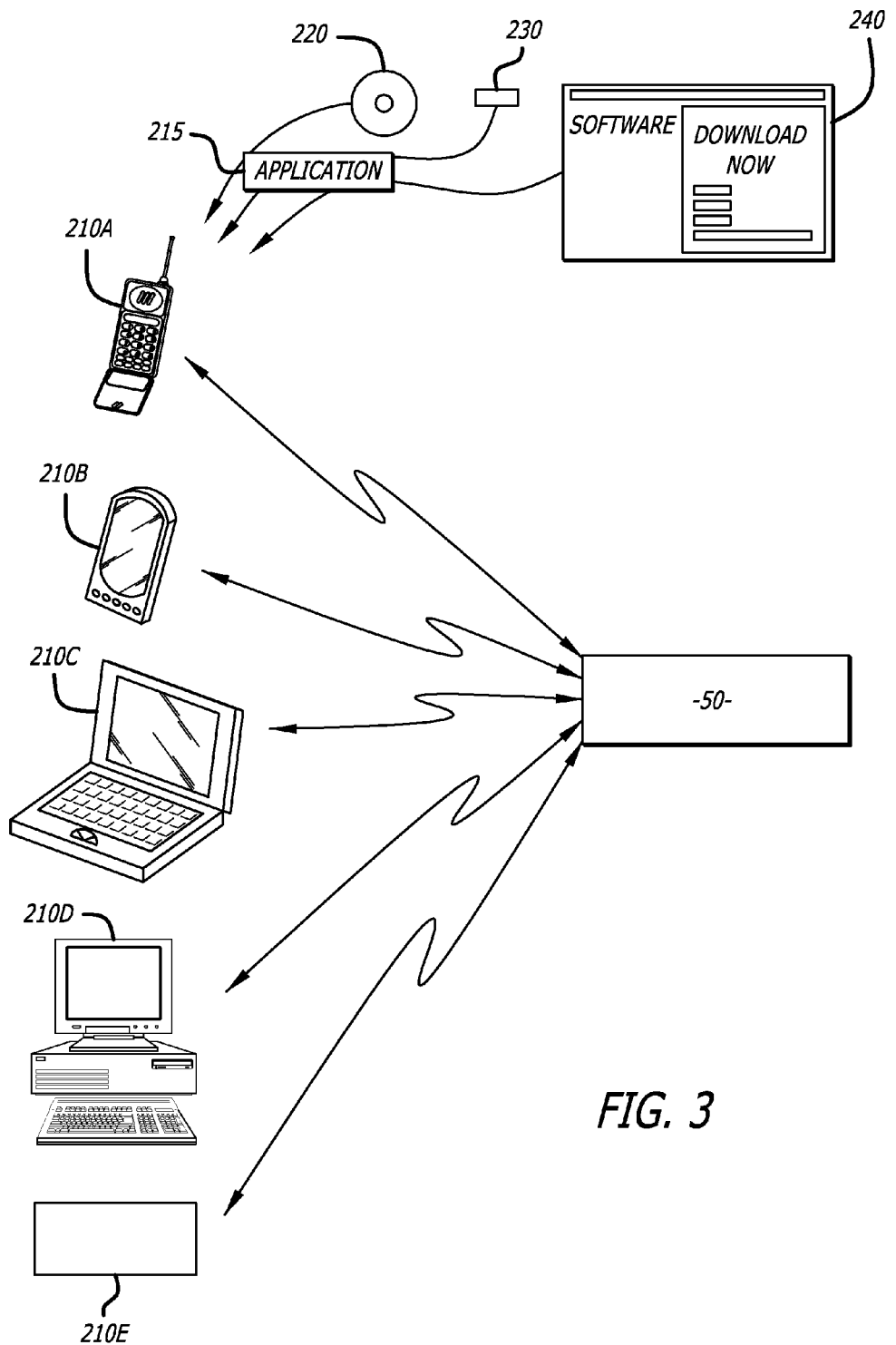
FIG. 3 is a block diagram of an exemplary glucose monitoring system showing a glucose monitor configured in accordance with FIG. 1, in wireless connection with a remote host calculation processor which may take the form of different types, as shown, and also showing an application program for execution by the remote host.

FIG. 3 is a block diagram of an exemplary blood glucose monitoring system consistent with certain aspects related to the invention. As shown in FIG. 3, implementations of the innovations herein include use of a blood glucose device 50 in connection with a variety of other components. As shown by way of illustration and not limitation in FIG. 3, for example, illustrative systems and methods may include operation of the blood glucose device 50 with a remote second/host computing device 210, such as a mobile phone 210A, a portable/personal computing device 210B such as a PDA, a portable computer 210C such as a laptop, a stand-alone or desktop computer 210D, or other computing devices (such as smart game consoles and others) 210E. Such second/host computing devices 210 may have an appropriate application program 215 already installed, or the systems and methods herein may include providing such an application program via computer readable media 220 such as a CD-ROM, via other memory devices 230 such as digital media, flash drives, optical drives, etc., or via electronic communication such as wired or wireless transmission, e-mail, download over a network such as the Internet 240, or by other means. Once resident on the second/host computing device 210, such application programs may be utilized as set forth herein to acquire and/or process glucose data and other relevant data from the glucose monitor 50.

Figure 4:
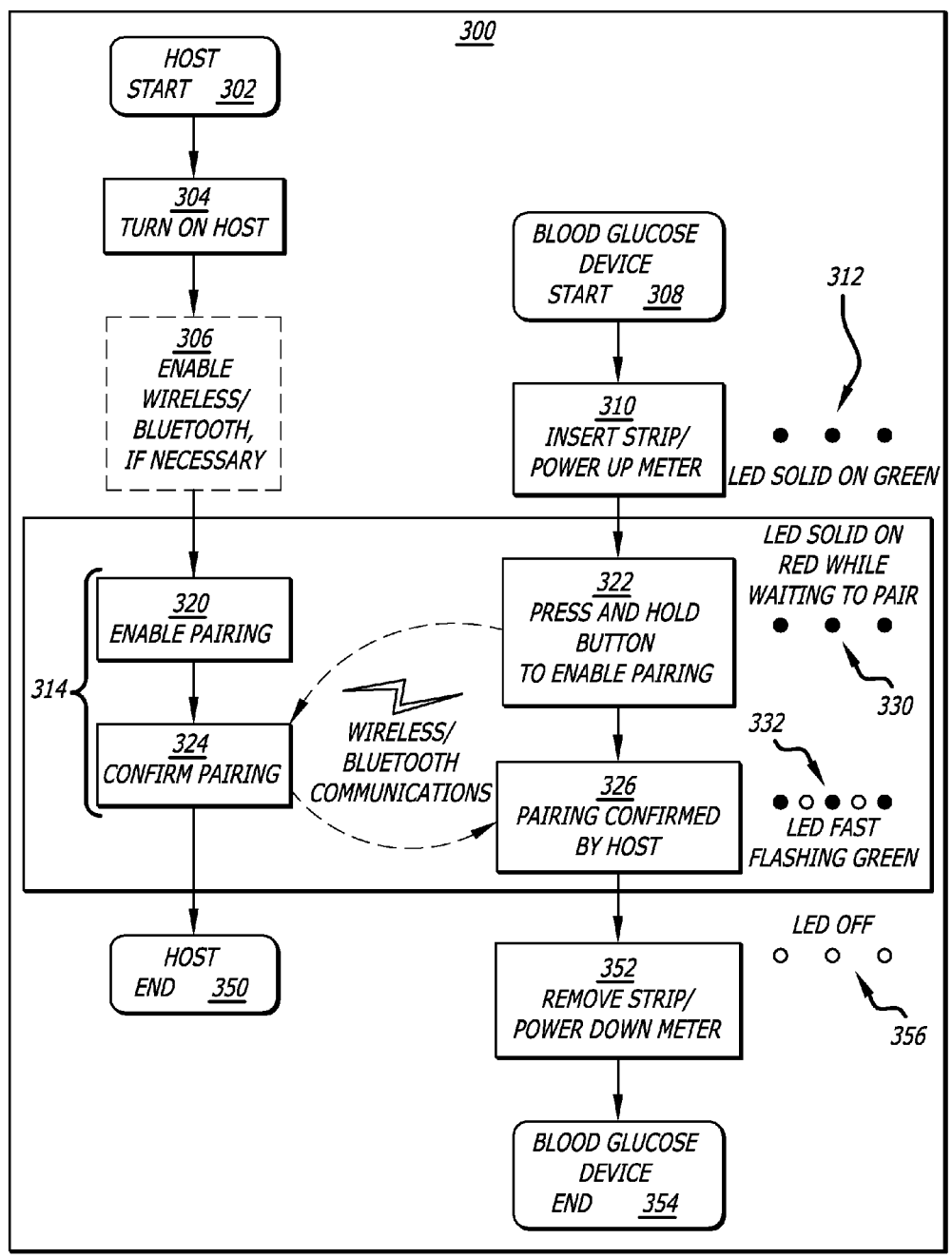
FIG. 4 is a flow diagram illustrating exemplary glucose data acquisition/processing functionality with wireless pairing between the glucose monitor and a remote host, and providing certain detail about a user interface on the glucose monitor.

FIG. 4 illustrates a flow diagram illustrating an exemplary glucose monitor and host pairing for data transfer consistent with certain aspects related to the innovations herein. As shown in FIG. 4, an exemplary method 300 may start 302 with a step of turning the host on or powering up the relevant circuitry 304. Further, the host device may also entail a step of initiating or enabling wireless/Bluetooth communications 306, although some host devices may have such wireless protocols running continuously. Similarly, the glucose monitor 100 may also perform start 308 and/or power up steps before it commences communication with the host device. In one exemplary implementation, the glucose monitor 100 then powers up 310. Here, for example, the glucose monitor 100 may be configured such that insertion of a glucose strip into the strip port 62 (FIG. 2) turns on/powers up the glucose device 100. Further, when the glucose device 100 is ready, an active or "on" state may be displayed via indicia such as a sequence or color of LEDs 312. Once the glucose device 100 and the host device 210 are configured for transmissions and receptions, a communication sequence 314 may be initiated to transmit the relevant data.

In an exemplary communication sequence 314, when the host device 210 (FIG. 3) is enabled 320 (e.g., for pairing, according to some protocols), a step of activating the glucose device to enable communication 322 may be executed. Here, for example, the glucose device 100 may be configured with a button 156 (FIG. 2) that a user may press/hold to enable communication or pairing. Further, an indicator 158 on the glucose device 100 may be included to provide status as to whether the link is established to the user. For example, the glucose device 100 may include LEDs that burn red 330 until the link is confirmed. Next, in steps 324 and 326, the host device 210 accepts the pairing and the glucose device 100 confirms the pairing so the relevant data may be transmitted between the glucose device 100 and the host device 210. Again, also by way of example, the glucose device 100 may include LEDs that blink in a specified sequence, color, etc. 332, such as fast flashing green lights, to indicate that pairing has occurred and/or communications are ongoing.

Finally, once all the relevant data has been transmitted, the host device 210 may perform appropriate end processes 350 to turn off or power down the relevant (e.g., communication) circuitry. Additionally, the glucose device 100 may perform similar end processes 352, 354 such as powering down the meter and/or electronics on the glucose device. In one exemplary end process 352, the glucose device 100 may be configured to power down by removal of the test strip from the reader port 62. To indicate that the communication link is closed and processing complete, the glucose device may, e.g., turn off one or more LEDs used to provide user output. While LEDs are illustrated as the indicators used to display information to the user in the examples herein, any other suitable (e.g., low cost) visual, audible, and tactile indicators may be used.

In other exemplary functionality bearing relation to FIG. 4, a streamlined method of acquiring blood glucose data may simply comprise turning on a host device and enabling pairing, inserting a test strip into a glucose device meter to power it up, thereby activating the glucose device to enable completion of pairing, accepting pairing on host device and receiving the desired data, and removing the test strip to power down the glucose device. This is particularly relevant to the embodiment of FIG. 1 because the monitor in that embodiment has not direct user control interface.

Figure 5:
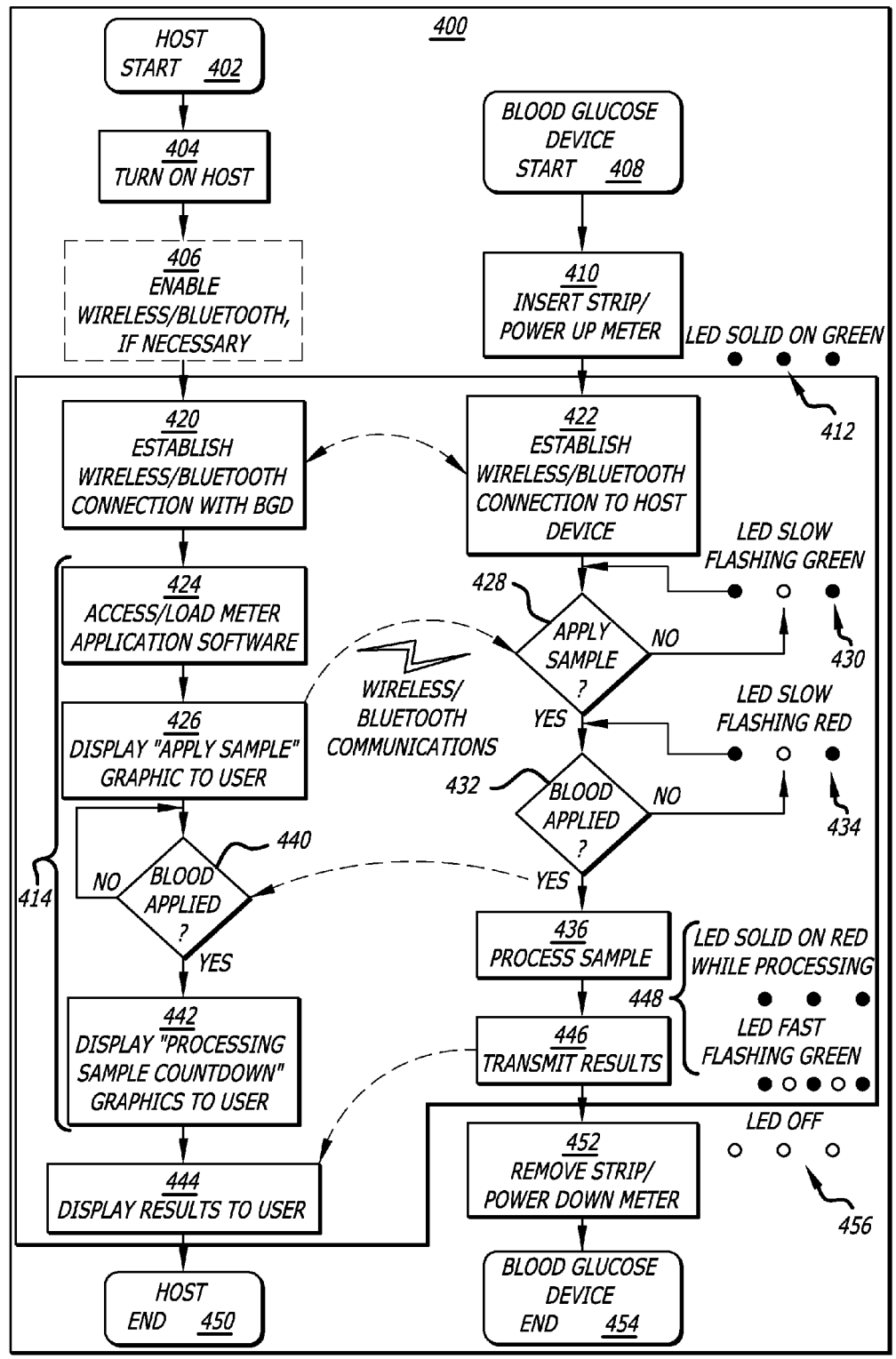
FIG. 5 is a flow diagram illustrating exemplary glucose data acquisition/processing functionality and wireless pairing consistent with certain aspects, also showing a passive user interface comprising light emitting diodes.

FIG. 5 illustrates a flow diagram illustrating exemplary glucose data pairing and data acquisition/processing functionality consistent with certain aspects related to the innovations herein. As shown in FIG. 5, an exemplary method 400 may include a step of turning the host on or powering up the relevant circuitry 404. Further, the host device may also require a step of initiating or enabling wireless/Bluetooth communications 406, although some host devices may have such wireless protocols running continuously. Similarly, the blood glucose monitor 100 (FIG. 2) may also require start 408 and/or power up steps before it commences communication with the host 210. In one exemplary implementation, the glucose monitor 100 is configured such that insertion of a glucose strip into the strip port turns on/powers up the glucose monitor 100 through activation of the switch 72. Further, when the glucose device 100 is ready, an active or "on" state may be displayed via indicia such as a sequence or color of LEDs 412. Once the glucose device 100 and the host device 210 are configured (paired) for transmissions, a communication sequence 414 may be initiated to transmit the relevant data.

In an exemplary communication sequence 414, when the host device 210 is enabled to establish wireless communication 420 (e.g., for pairing, according to some protocols), a step of establishing wireless/Bluetooth connectivity 422 at the glucose device may also be executed. Here, for example, the glucose device 100 may be configured with a button 156 (FIG. 2) that a user may press/hold to enable communication or pairing. Further, an indicator 158 on the glucose device 100 may be included to provide status regarding the link and associated communications to the user. For example, the glucose device 100 may include LEDs that blink in a slow flashing green pattern 430 until communication of glucose data begins.

Next, in step 424, the glucose monitor application software is accessed from within or loaded into the host device. The software may then display indicia on the host device 210 (FIG. 3) requesting that the user apply a glucose sample to the glucose device 426. A first determination step may then be performed 428, wherein the exemplary process asks/determines whether a sample was applied. If not, the previous indicia 430 will be displayed. If so, the display may be changed 434 (e.g., to slow, flashing red LEDs) and a second determination step is made, wherein the process asks/determines whether blood has been applied 432. If not, the display remains in the previous state 434. If blood has been applied, however, the host device may confirm this via another determination step 440, and then display a sample processing "count-down" graphic to the user 442. During this time, the glucose device processes the sample 436 and then transmits the results 446 to the host device, whereupon the host device displays the results to the user 444. And again, in one exemplary LED display implementation, the LEDs may be used to indicate this processing sample step 436 (e.g., solid red LEDs) as well as, then, the transmitting step 446 (e.g., fast flashing green LEDs).

Finally, once all the relevant data has been transmitted, the host device 210 may perform appropriate end processes 450 to turn off or power down the relevant circuitry. Additionally, the glucose device 100 may perform similar end processes 452, 454 such as powering down the meter and/or electronics on the glucose device. In one exemplary end process 452, the glucose device 100 may be configured to power down by removal of the strip from the reader 62. To indicate that the communication link is closed and processing complete, the glucose device may turn off one or more LEDs used to provide user output.

According to further exemplary implementations, a streamlined method of processing blood glucose data consistent with FIG. 5 may comprise inserting a test strip into a glucose device to power up the glucose device, establishing a communication link with a host device, executing, at the host device, a glucose monitoring application, obtaining a blood glucose sample from a user (or indicating to a user via a display that a blood glucose sample is desired, then obtaining the sample), informing the host device that the sample has been acquired, commencing processing the sample, indicating to the user that the sample is being processed, transmitting the results to the host device, and providing an output of glucose information for display to the user. Such methods may also include steps such as removing the strip from the glucose device, breaking the connection of the glucose device from the host device and powering the glucose device down, and continuing use of the host device to view one or more of result, review logs, graph results, etc.

Figure 6:
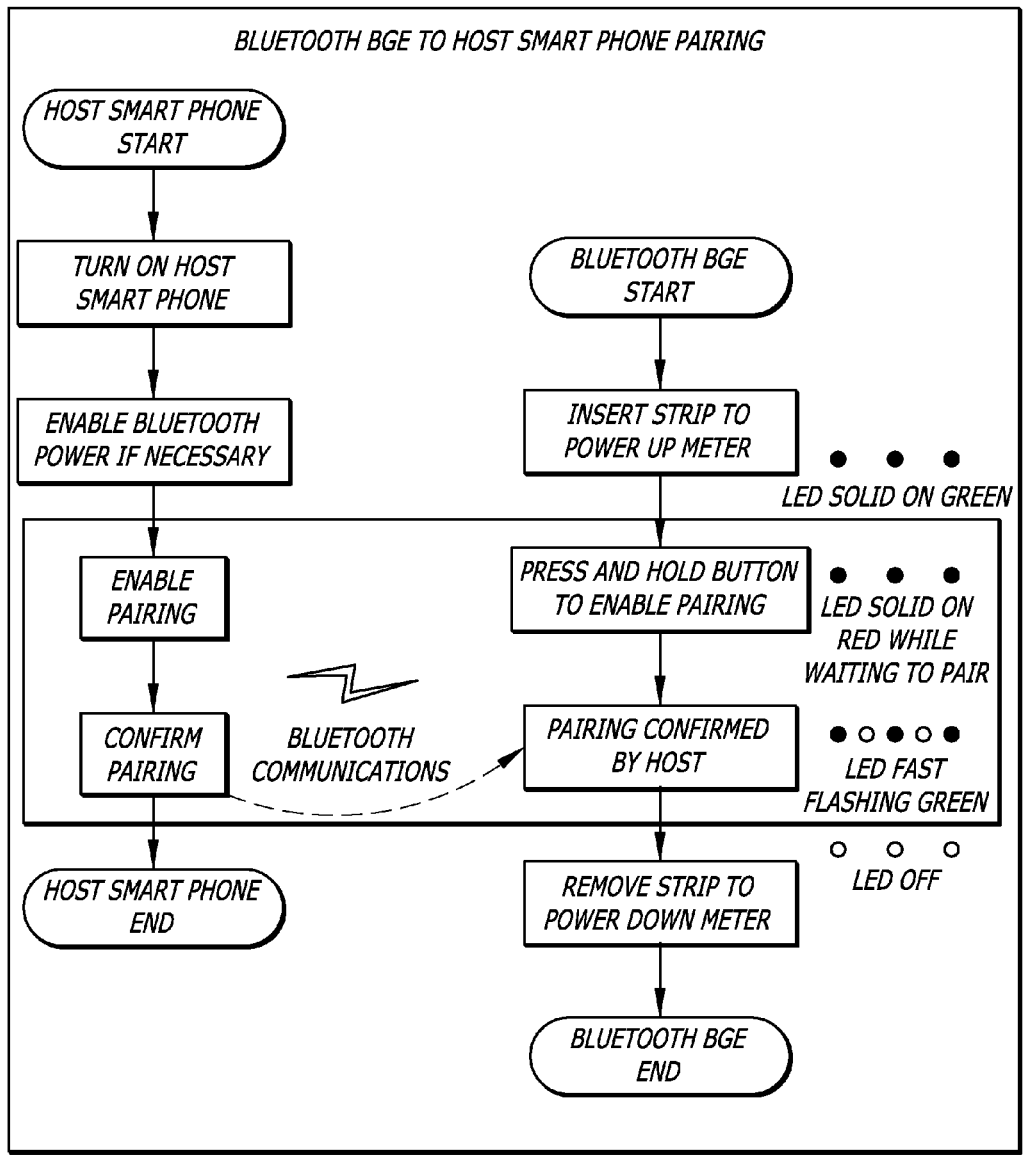
FIG. 6 is a flow diagram related to the flow diagram of FIG. 4 showing that the host takes the form of a smart phone, and providing aspects of pairing between the smart phone and the glucose monitor.

FIG. 6 is a flow diagram illustrating exemplary blood glucose monitor pairing with a smart phone, such as the Apple™ iPhone™. The FIG. 6 pairing method is closely similar to that of FIG. 4, though directed to illustrative Bluetooth implementations.

Figure 7:
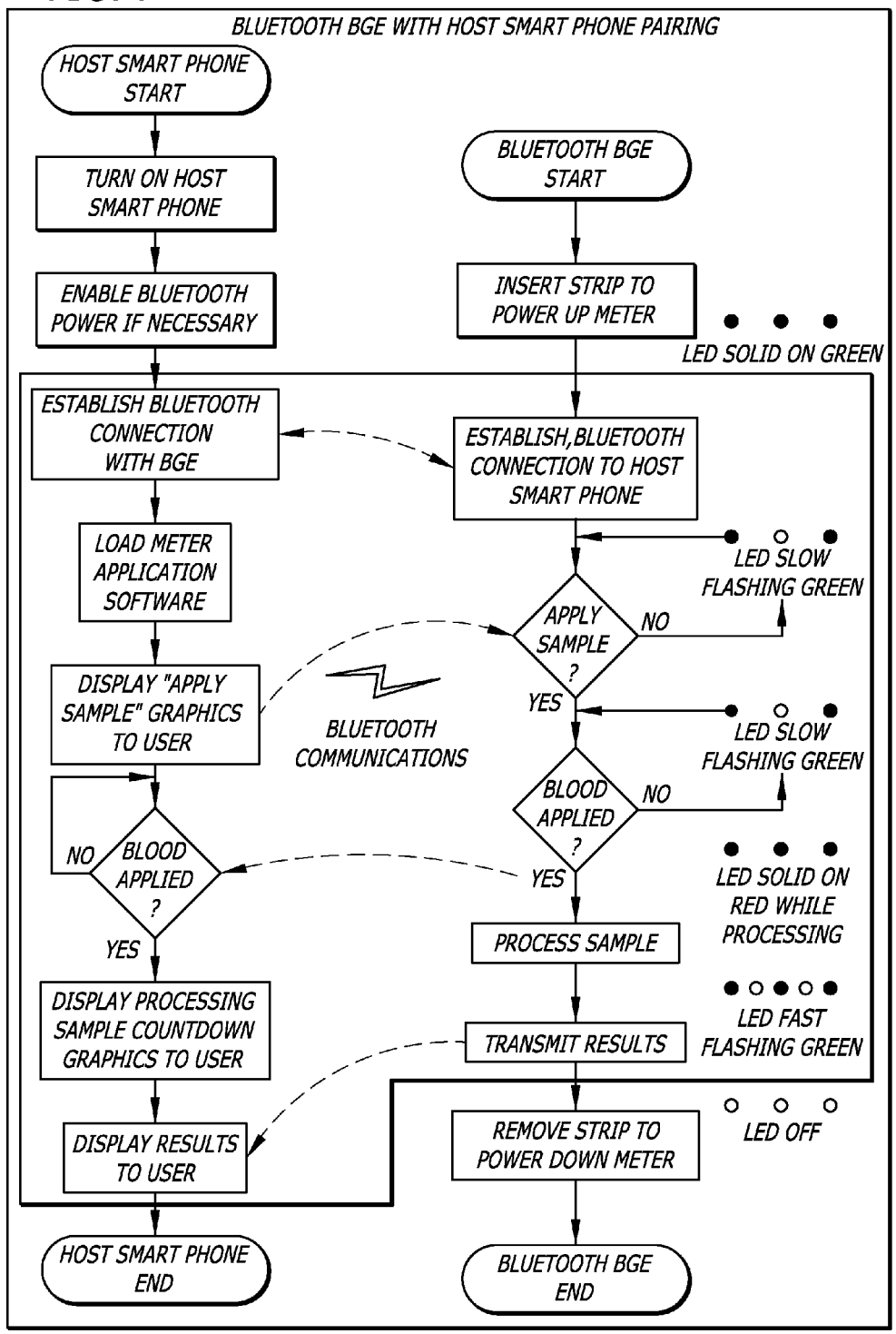
FIG. 7 is a flow diagram similar to FIG. 5 wherein the host takes the form of a smart phone, showing pairing between the smart phone and the glucose monitor, and a passive user interface wherein information is provided by the glucose monitor with light emitting diodes.

FIG. 7 is a flow diagram illustrating exemplary host and glucose monitor pairing and glucose data acquisition and/or processing functionality consistent with certain aspects related to the innovations herein. FIG. 7 illustrates exemplary blood glucose data acquisition/processing functionality closely similar to that of FIG. 5, though again directed to an Apple™ iPhone™ as a smart phone embodiment, and illustrative Bluetooth implementations. As shown herein in FIGS. 4-7, the smart phone embodiment may take the form of an Apple™ iPhone™.

In the present description, the terms component, module, device may refer to any type of logical or functional process or blocks that may be implemented in a variety of ways. For example, the functions of various blocks can be combined with one another into any other number of modules. Each module can be implemented as a software program stored on a tangible memory (e.g., random access memory, read only memory, CD-ROM memory, hard disk drive) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, embodiments and features of the invention may be implemented through computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe components such as software, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various processes and operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein may be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various functions disclosed herein may be described using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, and so on).

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

There has thus been provided a glucose monitor and monitoring system in which the glucose monitor cost has been minimized by shifting the user interface application, the memory, the display, and other functions to an existing smart hose device, which allows the glucose monitor (meter) to be smaller. The monitor may also now be made lighter which will be attractive to a large number of users. This will also allow the glucose monitor to be less complex due to fewer parts thereby lowering the cost, and may result in its becoming disposable after a certain number of uses.

Other embodiments of the invention will be apparent to those skilled in the art from consideration of the specification and practice of the invention disclosed herein. It is intended that the specification and examples be considered as exemplary only, with a true scope and spirit of the invention being indicated by the disclosure above in combination with the following paragraphs describing the scope of one or more embodiments of the following invention.

What is claimed is:

1. A diabetes management system comprising:
 a portable glucose monitor including:
  a glucose sensor that senses a glucose level and provides glucose sensor data representative of the level of glucose sensed;
  a glucose monitor processor configured to receive the glucose sensor data, process the received glucose sensor data, and provide such processed glucose data for transmission;
  a wireless communication component including a transmitter configured to receive the processed glucose data and wirelessly transmit the processed glucose data by a non-proprietary protocol;

a test strip switch located and configured to be activated by insertion of a test strip into the portable glucose monitor, the test strip switch providing an activation signal once activated;

wherein the glucose monitor processor is connected to the test strip switch and is programmed to become active upon receiving the activation signal at which time the glucose monitor processor receives the glucose senor data and provides the processed glucose data for transmission, and controls the wireless communication component to transmit the processed glucose data;

a portable housing in which are located only the glucose sensor, the glucose data processor, and the communication component and including no direct user interface other than the glucose sensor; and a remote host calculation device including:

a remote host communication module configured to wirelessly pair with the portable glucose monitor using the non-proprietary protocol so that data communications between the two may occur;

a display;

a remote host processor; and a nonvolatile memory in which is stored a host glucose data processing program;

wherein the remote host processor is connected to the remote host communication module; the display, and the remote host nonvolatile memory to access the memory to upload into the processor and run the host glucose data processing program which programs the remote host processor to:

control the remote host communication module to pair with the portable glucose monitor and receive processed sensor data;

analyze glucose data received from the portable glucose monitor;

display a determined glucose level; and provide a calculated action on the display in response to the determined glucose level.

2. The diabetes management system of claim 1, wherein the calculated action displayed by the host program includes a recommended dose of medication.

3. The diabetes management system of claim 1, wherein the glucose processing program further programs the remote host processor to time and date stamp the glucose data received.

4. The diabetes management system of claim 1, wherein the remote host calculation device comprises a smart phone having the host glucose data processing program as a downloadable application program.

5. The diabetes management system of claim 1, further comprising an input element configured to allow a user to input a manual coding for a test strip, wherein the host glucose data processing program further programs the remote host processor to analyze glucose data received from the portable glucose monitor in relation to the manual coding.

6. The diabetes management system of claim 1, wherein the portable glucose monitor includes no user interface other than a test strip reader.

7. The diabetes management system of claim 6, wherein the remote host calculation device further comprises a wireless pairing program configured to enable the remote host calculation device to perform a complete pairing procedure with the portable glucose monitor that has no pairing switch.

8. The diabetes management system of claim 6, wherein: the glucose monitor processor is further programmed, such that upon receipt of the activation signal, to automatically activate a wireless pairing feature in the portable glucose monitor to enable the portable glucose monitor to be paired with the remote host calculation device; and the host glucose data processing program further programs the remote host processor to perform a pairing procedure with the glucose monitor that is performing a pairing procedure when the test strip switch has been activated.

9. The diabetes management system of claim 1 wherein the non-proprietary wireless communication protocol is Bluetooth.

10. The diabetes management system of claim 1, wherein the portable glucose monitor further includes a temperature sensor configured to sense the temperature at the portable glucose monitor and provide a temperature data representative of the sensed temperature;

wherein the glucose monitor processor is further configured to receive the temperature data, process the received temperature data and provide such processed temperature data for transmission after activation;

wherein the wireless communication component is further configured to transmit the processed temperature data; and wherein the host glucose data processing program also programs the remote host processor to analyze the temperature data received from the portable glucose monitor in determining the glucose level.

11. The diabetes management system of claim 1 wherein:

the portable glucose monitor further includes a button and an indicator, the button when activated providing a pairing signal and the indicator providing a visual indicia of pairing;

the glucose monitor processor is further programmed, such that upon receipt of the pairing signal, to activate a wireless pairing feature in the portable glucose monitor to enable the portable glucose monitor to be paired with the remote host calculation device; and the indicator visually indicating the progress of pairing; and the host glucose data processing program further programs the remote host processor to perform a pairing procedure with the glucose monitor that is performing a pairing procedure when the button has been activated.

12. The diabetes management system of claim 11 wherein the indicator comprises a plurality of lights wherein the glucose monitor processor is configured to control the illumination of the lights to indicate the progress of pairing.

13. A diabetes management system comprising:

a portable glucose monitor including:

a glucose sensor that senses a glucose level and provides glucose sensor data representative of the level of glucose sensed;

a glucose monitor processor configured to receive the glucose sensor data, process the received glucose sensor data, and provide such processed glucose data for transmission;

a wireless communication component including a transmitter configured to receive the processed glucose data and wirelessly transmit the processed glucose data by a non-proprietary protocol;

a test strip switch located and configured to be activated by insertion of a test strip into the portable glucose monitor, the test strip switch providing an activation signal once activated;

wherein the glucose monitor processor is connected to the test strip switch and is programmed to become active upon receiving the activation signal at which time the glucose monitor processor receives the glucose sensor data and provides the processed glucose data for transmission, and controls the wireless communication component to transmit the processed glucose data;

wherein the glucose monitor processor is further programmed, such that upon receipt of the activation signal, to automatically activate a wireless pairing feature in the portable glucose monitor to enable the portable glucose monitor to be paired with the remote host calculation device;

a portable housing in which are located only the glucose sensor, the glucose data processor, and the communication component and including no direct user interface other than the glucose sensor; and a remote host calculation device including:
- a remote host communication module configured to wirelessly pair with the portable glucose monitor using the non-proprietary protocol so that data communications between the two may occur;
- a display;
- a remote host processor; and
- a nonvolatile memory in which is stored a host glucose data processing program;

wherein the remote host processor is connected to the remote host communication module; the display, and the remote host nonvolatile memory to access the memory to upload into the processor and run the host glucose data processing program which programs the remote host processor to:
- control the remote host communication module to pair with the portable glucose monitor and receive processed sensor data;
- analyze glucose data received from the portable glucose monitor;
- display a determined glucose level; and
- provide a calculated action on the display in response to the determined glucose level.

14. The diabetes management system of claim 13, wherein the calculated action displayed by the host program includes a recommended dose of medication.

15. The diabetes management system of claim 13, wherein the glucose processing program further programs the remote host processor to time and date stamp the glucose data received.

16. The diabetes management system of claim 13, wherein the remote host calculation device comprises a smart phone having the host glucose data processing program as a downloadable application program.

17. The diabetes management system of claim 13, further comprising an input element configured to allow a user to input a manual coding for a test strip, wherein the host glucose data processing program further programs the remote host processor to analyze glucose data received from the portable glucose monitor in relation to the manual coding.

18. The diabetes management system of claim 13, wherein the portable glucose monitor includes no user interface other than a test strip reader.

19. The diabetes management system of claim 13, wherein the remote host calculation device further comprises a wireless pairing program configured to enable the remote host calculation device to perform a complete pairing procedure with the portable glucose monitor that has no pairing switch.

20. The diabetes management system of claim 13, wherein the portable glucose monitor further includes a temperature sensor configured to sense the temperature at the portable glucose monitor and provide a temperature data representative of the sensed temperature;

wherein the glucose monitor processor is further configured to receive the temperature data, process the received temperature data and provide such processed temperature data for transmission after activation;

wherein the wireless communication component is further configured to transmit the processed temperature data; and wherein the host glucose data processing program also programs the remote host processor to analyze the temperature data received from the portable glucose monitor in determining the glucose level.

21. The diabetes management system of claim 13 wherein:
the portable glucose monitor further includes a button and an indicator, the button when activated providing a pairing signal and the indicator providing a visual indicia of pairing;

the glucose monitor processor is further programmed, such that upon receipt of the pairing signal, to activate a wireless pairing feature in the portable glucose monitor to enable the portable glucose monitor to be paired with the remote host calculation device; and the indicator visually indicating the progress of pairing; and the host glucose data processing program further programs the remote host processor to perform a pairing procedure with the glucose monitor that is performing a pairing procedure when the button has been activated.

22. The diabetes management system of claim 21 wherein the indicator comprises a plurality of lights wherein the glucose monitor processor is configured to control the illumination of the lights to indicate the progress of pairing.

* * * * *